(12) United States Patent
Schroer et al.

(10) Patent No.: US 11,319,291 B1
(45) Date of Patent: May 3, 2022

(54) CONTINUOUS FLOW MICROFLUIDIC PROCESS FOR SYNTHESIS OF 3,4-DINITROPYRAZOLE

(71) Applicant: Government of the United States, as represented by the Secretary of the Air Force, Wright-Patterson AFB, OH (US)

(72) Inventors: Thorsten G. Schroer, Palmdale, CA (US); Gregory E. Lecroy, Lancaster, CA (US); Mayra P. Rodriguez, Lancaster, CA (US); Sida Wang, Lancaster, CA (US); Miguel Aguila, Palmdale, CA (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 228 days.

(21) Appl. No.: 16/896,293

(22) Filed: Jun. 9, 2020

(51) Int. Cl.
  *C07D 231/38* (2006.01)
  *B01J 19/00* (2006.01)
(52) U.S. Cl.
  CPC ........ *C07D 231/38* (2013.01); *B01J 19/0093* (2013.01); *B01J 2219/00862* (2013.01)

(58) Field of Classification Search
  CPC ................ C07D 231/38; B01J 19/0093; B01J 2219/00862
  See application file for complete search history.

(56) References Cited

U.S. PATENT DOCUMENTS

| | | | |
|---|---|---|---|
| 3,487,087 | A | 12/1969 | Sarett |
| 4,621,157 | A | 11/1986 | McDaniel |
| 5,763,697 | A | 6/1998 | Hermann |
| 6,881,527 | B2 | 3/2005 | Fabian |
| 2004/0133046 | A1 | 7/2004 | Highsmith |
| 2008/0045722 | A1 | 2/2008 | Rajaraman |
| 2009/0298139 | A1 | 12/2009 | Zou |

OTHER PUBLICATIONS

Machine translation of Li, Patent document CN10225007.
Machine translation of Sakamoto, Patent document WO1996019470.

*Primary Examiner* — Alicia L Otton
(74) *Attorney, Agent, or Firm* — AFMCLO/JAZ; Timothy M. Barlow

(57) ABSTRACT

Disclosed herein is a synthetic method, apparatus, and system for the continuous-flow synthesis of 3,4-dinitropyrazole from pyrazole in a microfluidic environment. This synthetic strategy consist of three (3) synthetic steps, including (1) N-nitration of pyrazole, (2) thermal rearrangement into 3-nitropyrazole, and (3) 4-nitration of 3-nitropyrazole. The current technique produces 3,4-dinitropyrazole in yields up to 85% in particular embodiments, in comparison to 40-50% yields demonstrated by the current state of-the-art batch process for large scale synthesis from pyrazole.

25 Claims, 9 Drawing Sheets

CONTINUOUS FLOW MICROFLUIDIC PROCESS FOR SYNTHESIS OF 3,4-DINITROPYRAZOLE

RIGHTS OF THE GOVERNMENT

The invention described herein may be manufactured and used by or for the Government of the United States for all governmental purposes without the payment of any royalty.

Pursuant to 37 C.F.R. § 1.78(a)(4), this application claims the benefit of and priority to prior filed Provisional Application Ser. No. 62/880,148, filed 30 Jul. 2020, which is expressly incorporated herein by reference.

FIELD OF THE INVENTION

The present invention relates generally to a method of chemical synthesis and, more particularly, to a continuous flow microfluidic process for synthesis of 3,4-dinitropyrazole.

BACKGROUND OF THE INVENTION

Energetic materials have become increasingly more difficult to acquire within the United States for research and development purposes. Increased regulation on energetic materials have led to restricted supply chains and significantly inflated costs for purchasing and storing of these materials. Therefore, much interest has been demonstrated within the energetics community for safe on-site and on-demand methods and processes for the production of these energetic materials in appropriate quantities for consumption.

Recently, 3,4-dinitropyrazole has been a compound of interest within the energetics community, owing to the relatively low melting point and high thermal decomposition temperature; however, the current state-of-the-art synthesis for the large-scale production is quite tedious and labor intensive. This prior art procedure produces 3,4-dinitropyrazole from pyrazole in three steps, each of which require the work-up, isolation, and purification of each intermediate product. In addition, this process is chemically inefficient, producing only 25-50% yields from pyrazole. While other methods exist for the synthesis of 3,4-dinitropyrazole, these methods also require extensive workup and purification or expensive catalysts and are not feasible for scaling of production. Therefore, it is of great interest to the energetic community for the development of an alternate production process for the synthesis of 3,4-dinitropyrazole without the need for extensive purification and isolation of intermediates.

SUMMARY OF THE INVENTION

The present invention overcomes the foregoing problems and other shortcomings, drawbacks, and challenges of 3,4-dinitropyrazole production. While the invention will be described in connection with certain embodiments, it will be understood that the invention is not limited to these embodiments. To the contrary, this invention includes all alternatives, modifications, and equivalents as may be included within the spirit and scope of the present invention.

The present invention relates to the microfluidic processes and methods for the chemical synthesis of energetic materials and intermediates thereof. More specifically, the invention relates to a process for the synthesis of 3,4-dinitropyrazole from pyrazole and the corresponding intermediates, i.e. 1-nitropyrazole and 3-nitropyrazole, in a continuous-flow microfluidic reactor. Specifically, the invention relates to a process for a three-step continuous-flow transformation of pyrazole into 3,4-dinitropyrazole without the need for the separation and purification of reaction intermediates between the corresponding steps. In addition, this invention also relates to the microfluidic methods for producing the corresponding intermediates, i.e. 1-nitropyrazole and 3-nitropyrazole, and which may also be isolated.

According to a first embodiment of the present invention, a continuous flow microfluidic process comprises reacting a mixture of pyrazole and acetic anhydride with nitric acid in a first microreactor to yield a first reaction solution comprising 1-nitropyrazole. The process may be stopped there to collect the 1-nitropyrazole yield, or the continuous flow microfluidic process may be continued.

Alternatively, in a second embodiment, the continuous flow microfluidic process may further comprise thermally rearranging the 1-nitropyrazole in a second microreactor to yield a second reaction solution comprising 3-nitropyrazole. The process may be stopped there to collect the 3-nitropyrazole yield, or the continuous flow microfluidic process may be continued. The 1-nitropyrazole may be from the process described in the first embodiment herein, or may be derived from a different source.

In a third embodiment, the continuous flow microfluidic process of the second embodiment may further comprise reacting the 3-nitropyrazole with a mixture of nitric acid and sulfuric acid in a third microreactor to yield a third reaction solution comprising 3,4-dinitropyrazole. The 3-nitropyrazole may be from the process described in the second embodiment herein, or may be derived from a different source.

In a variation of the continuous flow microfluidic process of the first embodiment, the acetic anhydride solution further comprises acetic acid. The molar ratios of pyrazole:acetic anhydride may be 1.0:1.0 to 2.0:1.0, or any desired range thereof. The reaction in the first microreactor may be performed between 20-50° C., between 20-30° C., or about 25° C. Optionally, the 1-nitropyrazole may be collected from the first microreactor and isolated, or the 1-nitropyrazole may be used in the continuous flow microfluidic process toward the synthesis of 3-nitropyrazole, 3,4-dinitropyrazole or another product. The molar ratio of nitric acid:pyrazole in the first microreactor may be 1.0:0.3 to 1.0:1.0, or any desired range thereof. The reaction in the first microreactor may be performed with a residence time of 0.17-10 minutes.

In a variation of the continuous flow microfluidic process of second embodiment, the thermal rearrangement is performed between 110-180° C., or any desired range thereof. Optionally, the 3-nitropyrazole may be collected from the second microreactor and isolated, or the 3-nitropyrazole may be used in the continuous flow microfluidic process toward the synthesis of 3,4-dinitropyrazole or another product. The thermal rearrangement may be performed between 110-180° C. for at least 15 minutes.

In a variation of the continuous flow microfluidic process of the third embodiment, the 3,4-dinitropyrazole may be collected from the third microreactor and isolated. The sulfuric acid may be concentrated, e.g. 98 wt %, and the nitric acid may be 100 wt %. The continuous flow microfluidic process of the third embodiment may further comprise performing the reaction of the 3-nitropyrazole with the mixture of nitric acid and sulfuric acid to yield 3,4-dinitropyrazole at 25-80° C. The molar ratio of nitric acid:sulfuric acid is 1.0:1.0 to 1:10, 1:5, or any subrange thereof. The reaction of the 3-nitropyrazole with the mixture of nitric acid and sulfuric acid in the third microreactor may include a residence time of 1-10 minutes.

In a further variation of the continuous flow microfluidic process of the third embodiment, the third reaction mixture, containing the 3,4-dinitropyrazole, may be diluted with deionized water and the 3,4-dinitropyrazole may be extracted with an immiscible organic solvent selected from the group consisting of chloroform, ethyl acetate, hexanes, and diethyl ether. The diluting and extracting steps with regard to the 3,4-dinitropyrazole may be performed in-flow.

Each or any of the first, second, and third microreactors may have an inside diameter of between 0.2-1.0 mm. Each or any of the first, second, and third microreactors may be made from any one of FEP (fluorinated ethylene propylene) tubing, FEP tubing with static helical mixers, and glass.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

Figure 1:
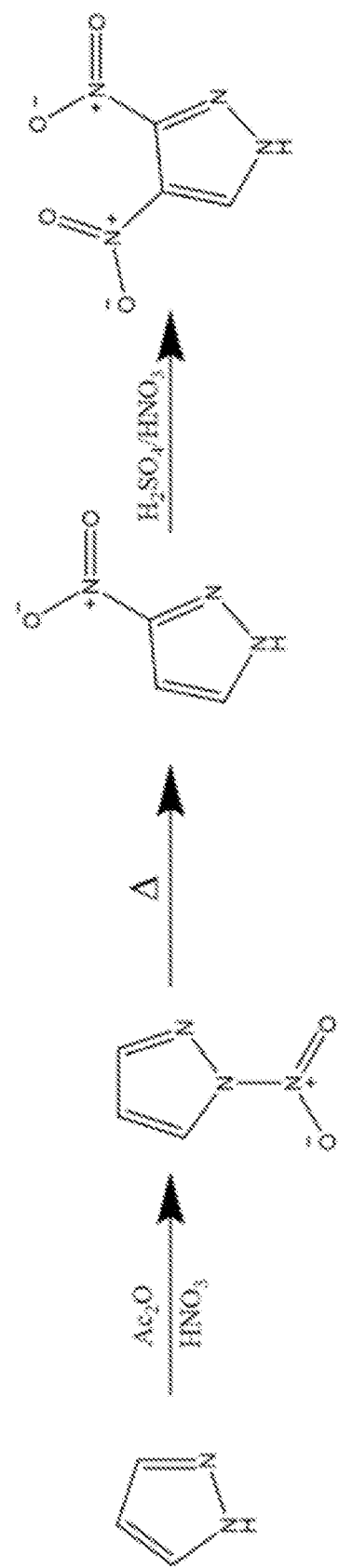
FIG. 1 presents a schematic representation for the chemical transformation of pyrazole into 3,4-dinitropyrazole, according to an embodiment of the invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

The present invention provides methods, apparatus, and systems for the synthesis of 3,4-dinitropyrazole from pyrazole, in which some or all of the steps involved in the chemical transformation are conducted in a microfluidic environment (i.e. in a microreactor), and which may be in a continuous, in-flow manner, or separated into a discrete step for each intermediate, i.e. 1-nitropyrazole and 3-nitropyrazole, and the final product, i.e. 3,4-dinitropyrazole, or certain reactions may be conducted in a batch reactor, i.e. thermal rearrangement of 1-nitropyrazole to 3-nitropyrazole. The prior synthesis of this compound has been as a wet-chemistry synthesis and required isolation and purification of the intermediates between all or some of the steps. The present invention presents a continuous-flow method, apparatus, and system for the synthesis of 3,4-dinitropyrazole and the corresponding intermediates (1-nitropyrazole and 3-nitropyrazole) without the need for isolation or purification of intermediates between each chemical transformation.

The synthesis of 3,4-dinitropyrazole in this microfluidic reaction design may include three transformations from pyrazole:

i) N-nitration of pyrazole by acetic anhydride and nitric acid mixtures, ii) thermal rearrangement of reaction mixture from the N-nitration of pyrazole in a residence loop reactor, or in a neat 1-nitropyrazole melt in a batch reactor and iii) mixed acid nitration of 3-nitropyrazole to yield 3,4-dinitropyrazole.

The presented process provides a marked improvement over the current state-of-the-art batch synthesis because there is no need for isolation and purification of intermediate species between reaction steps, and the corresponding reaction yield up to 85% in particular embodiments in comparison to 40-50% yield demonstrated in the current state-of-the art batch process from pyrazole. In the presented method, there is no need for isolation of intermediate species from the reaction medium between sequential steps since the subsequent transformations are made in the presence of the existing reacting mixture, while retaining good to excellent product yields. Additionally, this process may be scaled linearly by increasing the time the microfluidic reactor is operated or by running several microreactors in parallel, without suffering from the scaling challenges observed in the aforementioned batch processes.

Generally, continuous-flow production methods are prohibitively expensive to develop and implement and require equipment dedicated to a single synthesis, however, with the onset of microfluidic technologies, a continuous-flow synthesis is affordable while retaining the flexibility of batch reactors. Microfluidic technology initially gained prominence within the pharmaceutical industry in the 1990s. In comparison to a typical batch process, microfluidic reactions take place in micro-channels having inner dimensions, e.g. inside diameters, less than 1 mm. The higher surface area to volume ratios in comparison to a traditional batch process allows for precise temperature control and/or greatly improved heat transfer for highly exothermic reactions. Due to the improved heat transfer characteristics, microfluidic reactions may utilize reagents having much higher concentrations than their batch process counterparts, which drastically cuts down on the costs associated with the generation and disposal of reaction waste products, as well as increasing the production rate for a chemical reaction. Improved heat transfer also allows for safer operation for the synthesis of high energy density materials since only a small portion of the material is within the "reaction zone" at a time, in which the reaction zone is defined as the area in which all or most of the chemical transformations are occurring.

The production scaling for microfluidic reactions is also significantly easier than scaling a production process developed as a batch synthesis. While large-scale production using traditional batch synthesis techniques relies on increasing the volume of the reaction mixture, microfluidic reactions scale linearly; more material may be produced by simply increasing the run-time for a given process or by running several reactions on parallel microfluidic reactors. The ease of scaling for microfluidic processes eliminates the need for intensive optimizing when increasing production from milligrams to kilograms.

The small size of a microreactor allows for a smaller reactor footprint, drastically reducing infrastructure costs as well as allowing for the easy shipping and transport of reactor components for onsite synthesis, e.g. where the end product will be consumed. Flexibility in the transport of the microfluidic reactor allows for the synthesis on-demand of materials, in which the material is synthesized in quantities that will be consumed, cutting down on handling and storage costs associated with energetic materials.

For the synthesis of 3,4-dinitropyrazole, the prior art wet-chemistry batch process for the production of 3,4 dinitropyrazole was translated into a microfluidic reaction design. Embodiments of the present disclosure provide processes and methods for the continuous-flow synthesis of 3,4-dinitropyrazole, systems for making 3,4-dinitropyrazole, as well as devices including the 3,4-dinitropyrazole formed using these methods and systems, and the like.

The transformations (i-iii) described above may be achieved within a continuous-flow microfluidic process and apparatus, and the intermediates may be collected and isolated for use in further transformations or for other desired synthesis goals. Particularly, in one embodiment, step (i) may be conducted individually to yield high purity 1-nitropyrazole without the need for extensive post-reaction purification. In another embodiment, steps (i) and (ii) may be conducted sequentially to yield 3-nitropyrazole. Steps (i-iii) may be performed in sequence to yield 3,4-dinitropyrazole. In the alternative, each of the 1-nitropyrazole and 3-nitropyrazole may be sourced independently or processed in separate apparatuses, and may be microfluidically processed, as described herein, to achieve 3-nitropyrazole and/or 3,4-dinitropyrazole, respectively, as desired.

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

In detail, the present invention pertains to processes, methods, and apparatuses for the continuous-flow microfluidic synthesis of 3,4-dinitropyrazole from pyrazole, and the corresponding intermediates thereof. In a particular embodiment, each subsequent chemical transformation may be conducted in the reaction mixture of the previous chemical transformation without the need for separation, isolation, or purification of each intermediate species from by products or solvents generated in the previous steps.

Specifically, the steps described herein can be viewed discretely as follows:
(1) N-nitration of pyrazole in acetic acid/acetic anhydride mixtures or in neat acetic anhydride (see FIGS. 1, 2, and 4),
(2) thermal rearrangement of the resulting 1-nitropyrazole (1-NP) reaction mixture to 3-nitropyrazole (3-NP) (see FIGS. 1, 2, and 6), or thermal rearrangement of a neat 1-NP melt in a batch reactor and
(3) 4-nitration of the previously produced 3-nitropyrazole by mixed nitric acid and sulfuric acid (see FIGS. 1, 2, and 8).

Figure 2:
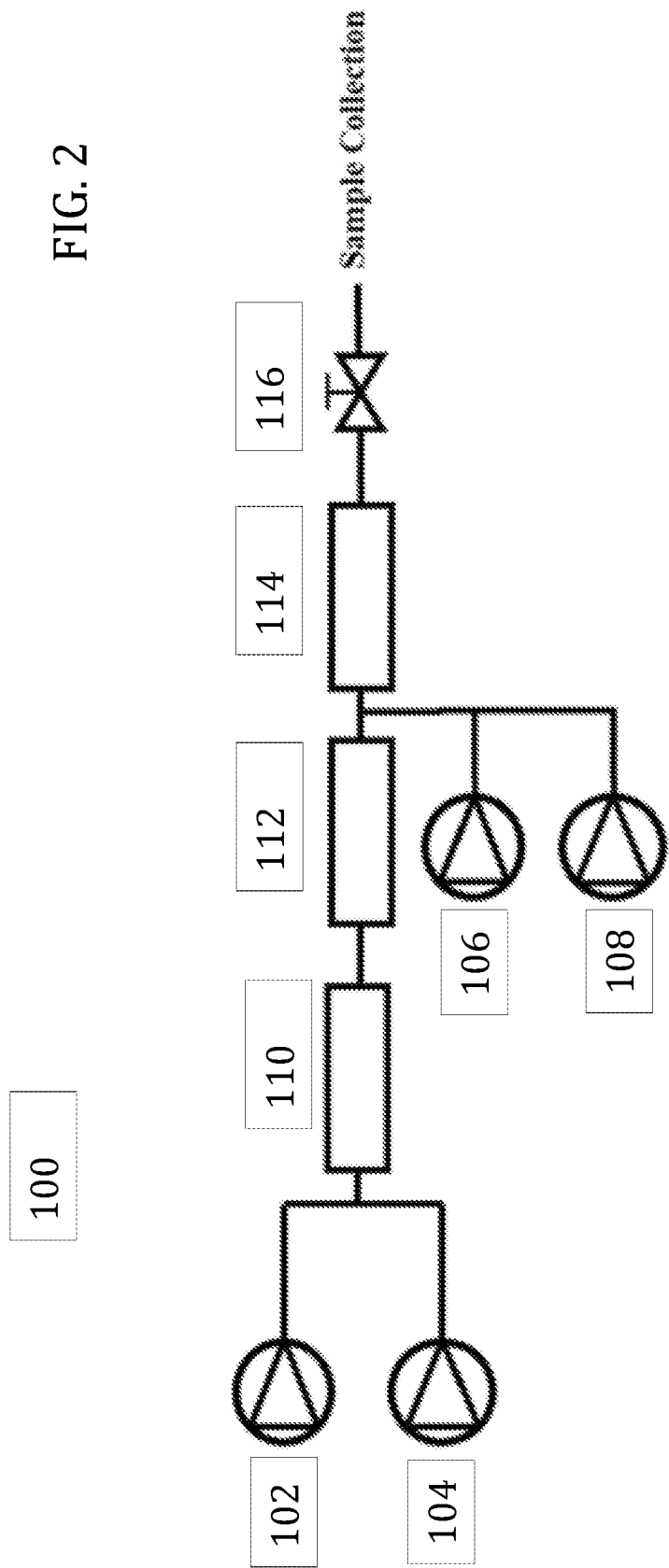
FIG. 2 illustrates a microfluidic reactor for the continuous flow synthesis of 3,4-dinitropyrazole from pyrazole, according to an embodiment of the invention.

A schematic representation of these chemical transformations is presented in FIG. 1. The microfluidic reaction design for the synthesis of 3,4-dinitropyrazole may be understood as a linear combination of the individual reactions described as chemical transformations (1)-(3) in the previous paragraph. In a particular embodiment, a reagent for each subsequent transformation is the product from the previous step and each process is in fluidic communication with all upstream and downstream processes. In a specific embodiment of this process, an example of the microfluidic reactor 100 used in the transformation of pyrazole into 3,4-dinitropyrazole is illustrated in FIG. 2. In one embodiment, the continuous-flow microfluidic reactor 100 may be equipped with four (4) syringes, each equipped with a corresponding syringe pump, in which the syringe and syringe pump combinations (syringe/pump) are designated as 102, 104, 106, 108 within FIG. 2. In this particular embodiment, each of the syringe pumps 102-108 presented in FIG. 2 contains specific reagents and/or reagent/solvent mixtures. Specifically, syringe/pump 102 is designated for nitric acid, syringe/pump 104 for a pyrazole/acetic acid/acetic anhydride solution or a pyrazole/acetic anhydride solution, syringe/pump 106 for sulfuric acid, and syringe/pump 108 for nitric acid.

In a particular embodiment, syringes designated for nitric acid and sulfuric acid contain solutions of concentrated acids, specifically, 100 wt % nitric acid and 98 wt % sulfuric acid. Each of the reactions which occur during the transformation of pyrazole into 3,4-dinitropyrazole occur within the corresponding microreactors 110, 112, 114 in FIG. 2. Each of these microreactors 110, 112, 114 includes an interior reaction zone in which the majority of the chemical transformations (1)-(3) occur and correspond to 110, 112, 114, respectively.

For these microreactors 110-114, several materials were found to be suitable for or compatible with the chemical transformations. For example, in particular embodiments, commercially available glass microreactors, FEP (fluorinated ethylene propylene) tubing, and FEP tubing equipped with a static helical mixer have been used successfully. The description of the microreactor's composition is provided as an example for particular embodiments of this invention, but should not be considered as limiting in the scope of this invention. The continuous-flow reactor 100 may also be equipped with a back pressure regulator 116, as designated in FIG. 2. Pressures for the back pressure regulator 116 may be 1 to 5 bar, and may preferably be set to 2 bar.

In a particular embodiment, the transformation of pyrazole to 1-nitropyrazole, which occurs within microreactor 110, may be conducted with reagent mixtures, in a particular embodiment, of pyrazole in neat acetic anhydride, which is presented as the solution contained within syringe/pump 104. Reactant mixtures may be prepared in molar ratios of 1.0:1.0 to 2.0:1.0 for acetic anhydride and pyrazole. In a particular embodiment, this mixture contained within syringe/pump 104 is reacted with 100 wt % nitric acid (syringe/pump 102) within microreactor 110. In a particular embodiment, the nitric acid and pyrazole/acetic anhydride solutions may be pumped into microreactor 112 through commercially available FEP tubing.

The reaction between the described reagents from syringe/pumps 102-104 may be conducted from room temperature (about 20° C.) to 50° C.; preferably the reaction is conducted at 20-30° C. or 25° C. For these reagents, molar ratios ranging from 1.0:0.3 to 1.0:1.0, for nitric acid and pyrazole, respectively, may be selected for the nitration process. This transformation may be achieved at a variety of flow rates between the nitric acid and pyrazole solutions, with residence times between 0.17 minutes to 10 minutes, depending on the volume of the microreactor 110. In a particular embodiment, for a 100 μL microreactor and a residence time of 1 minute, the flow rates for nitric acid and the pyrazole solution may be 17-46 and 54-83 μL/min, respectively. The composition of the microreactor 110 for the aforementioned transformation may be composed of a variety of materials. In particular embodiments, glass, FEP equipped with a static helical mixer, or FEP in the absence of a static helical mixer, or another material which is compatible with strongly acidic solutions may be used. In specific embodiments, the FEP tubing may have inner diameters of 0.2-1.0 mm.

Immediately following the N-nitration of pyrazole described in the previous paragraph, 3-nitropyrazole may be formed through the rearrangement of 1-nitropyrazole in this continuous-flow reaction operation by flowing the reaction solution from microreactor 110 into microreactor 112. In a particular embodiment, heat is applied to microreactor 112 at temperatures between 110° C. to 180° C. and residence times within microreactor 112 greater than 15 minutes. In a particular embodiment, microreactor 112 comprises FEP tubing with an internal diameter of 0.2-2.0 mm was sufficient for this transformation.

The subsequent production of 3,4-dinitropyrazole through the 4-nitration of 3-nitropyrazole produced in the previous step is achieved by mixed nitric acid/sulfuric acid nitration in microreactor 114. In a particular embodiment, the reaction mixture emerging from microreactor 112 is combined with the premixed nitric acid:sulfuric acid mixtures (from syringe/pumps 106, 108) with molar ratios ranging from 1:1 to 1:10, respectively. Preferably, the molar ratio of nitric acid:sulfuric acid is 1:5. The described reaction occurring within microreactor 114 in FIG. 2 may be conducted at temperatures between 25° C. to 80° C. The reacting solutions are generally reacted with a residence time within microreactor 114 between 1 min to 10 min. In a particular embodiment of this invention, microreactor 114 may be composed of glass.

Figure 3:
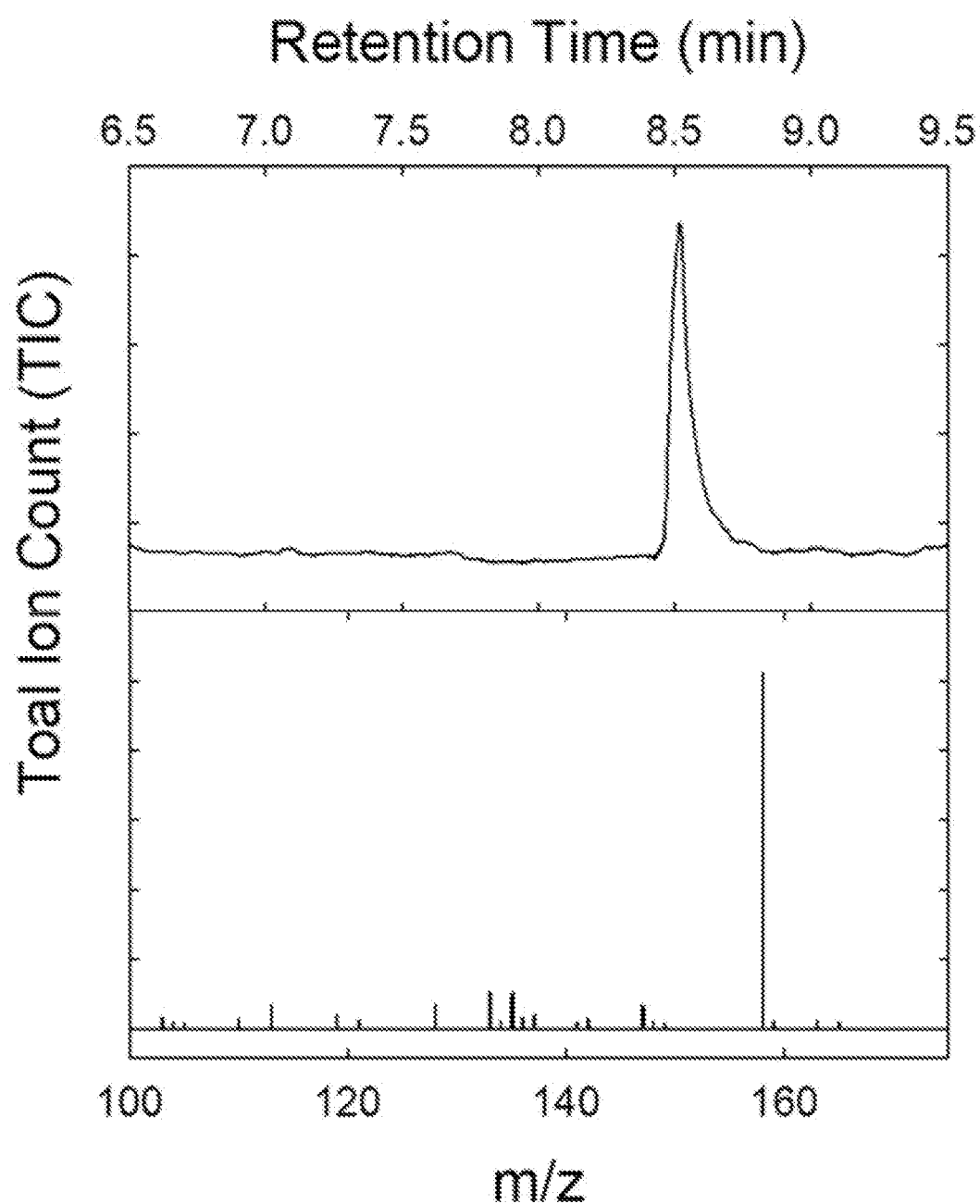
FIG. 3 presents a gas chromatogram (top) and mass spectrum (bottom) for 3,4-dinitropyrazole synthesis produced from the continuous flow reactor presented in FIG. 2.

The reaction mixture containing 3,4-dinitropyrazole (from microreactor 114) as produced by the 4-nitration of 3-nitropyrazole may be isolated in-flow or extracted manually with a suitable organic solvent. In a specific embodiment, the reaction solution from microreactor 114 may be diluted with deionized water and the 3,4 dinitropyrazole extracted with an immiscible organic solvent, such as chloroform, ethyl acetate, hexanes, or diethyl ether. The two-phase mixture, consisting of an aqueous waste phase and an organic phase containing 3,4-dinitropyrazole, may be separated by passing through an in-flow separator to collect the organic phase. A gas chromatogram and corresponding mass spectrum for 3,4-dinitropyrazole produced in a specific embodiment of the method described are presented in FIG. 3, in which 3,4-dintiropyrazole elutes at 8.5 minutes.

Figure 4:
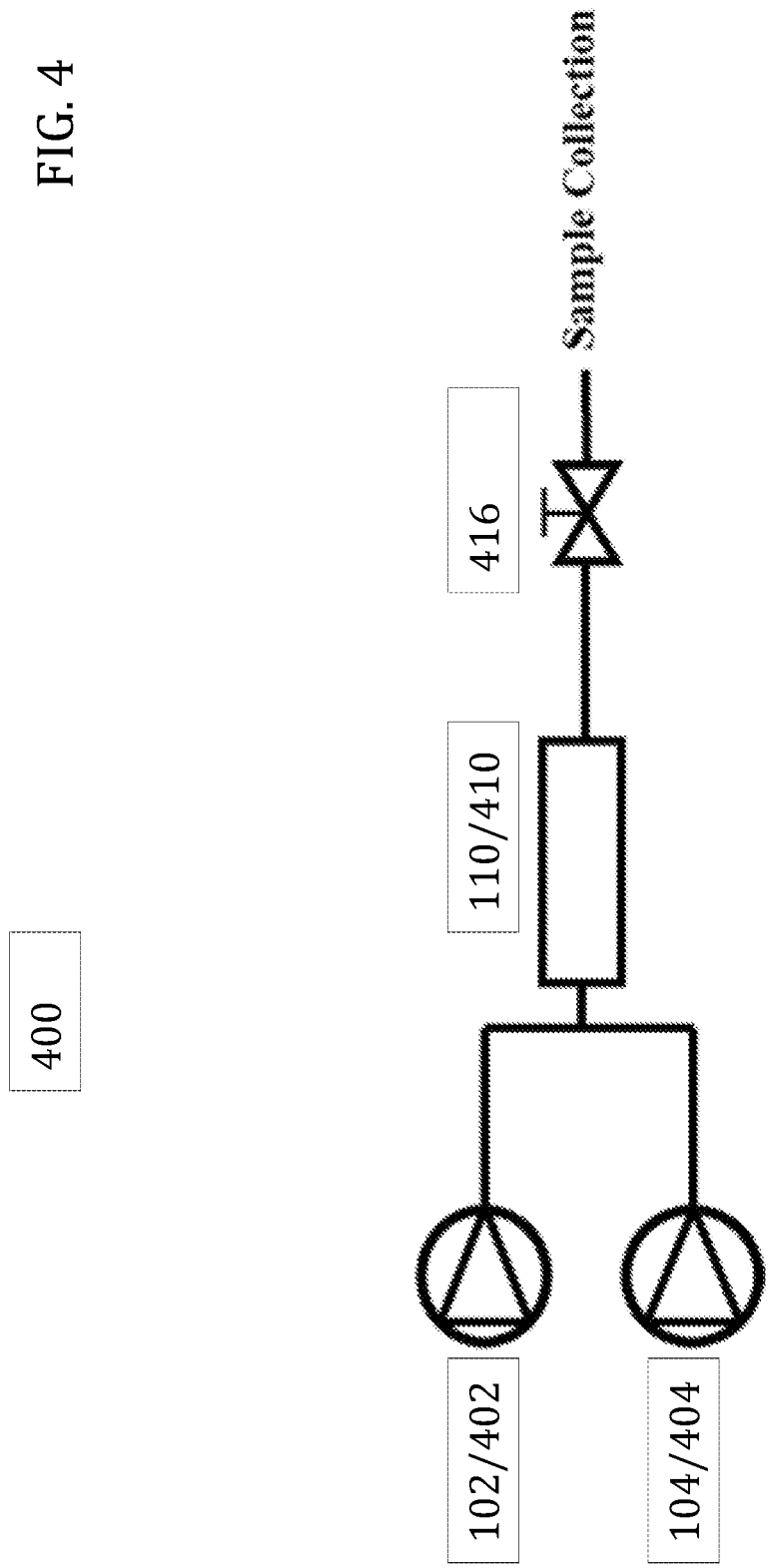
FIG. 4 presents a microfluidic reactor for the continuous flow synthesis of 1-nitropyrazole from pyrazole, according to an embodiment of the invention.

In addition to the continuous flow synthesis of 3,4-dinitropyrazole as described in the previous paragraphs, each of the intermediate species produced in this reaction, namely, 1-nitropyrazole and 3-nitropyrazole, may be isolated in good to excellent yields by excluding the downsteam transformations, as illustrated by the microfluidic design depicted in FIG. 4. Similar to the continuous-flow process described previously, the transformation of pyrazole to 1-nitropyrazole, which occurs within microreactor 110/410 as depicted in FIG. 4, may be achieved with pyrazole in neat acetic anhydride mixtures, which is represented as the solution contained within syringe/pump 102/402 in FIG. 4. Reactant mixtures may be prepared in molar ratios of 1.0:1.0 to 2.0:1.0 for acetic anhydride and pyrazole, respectively. In a particular embodiment, the aforementioned reaction mixture is reacted with 100 wt % nitric acid, which is delivered from syringe/pump 104/404 in FIG. 4. In a particular embodiment, nitric acid and pyrazole solutions are pumped into microreactor 110/410 at a temperature ranging from room temperature (about 20° C.) to 50° C., but preferably the reaction is conducted at between 20-30° C., or about 25° C. For these reagents, molar ratios ranging from 1.0:0.8 to 1.0:1.2, for nitric acid and pyrazole, respectively, were used, with residence times between 0.17 minutes to 10 minutes.

The composition of the microreactor 110/410 for the aforementioned transformation may be composed of a variety of materials. In particular embodiments, glass, FEP equipped with a static helical mixer, or FEP in the absence of a static helical mixer, or another material which is compatible with strongly acidic solutions have been used and are acceptable. The FEP tubing may have an inner diameter of 0.2-1.0 mm. The description of the microreactor composition is provided as an example for particular embodiments of this invention, but should not be considered as limiting in the scope of this invention. The microfluidic process design is equipped with a back pressure regulator 416, as depicted in FIG. 4, which may be set between 1 bar to 3.5 bar.

Figure 5:
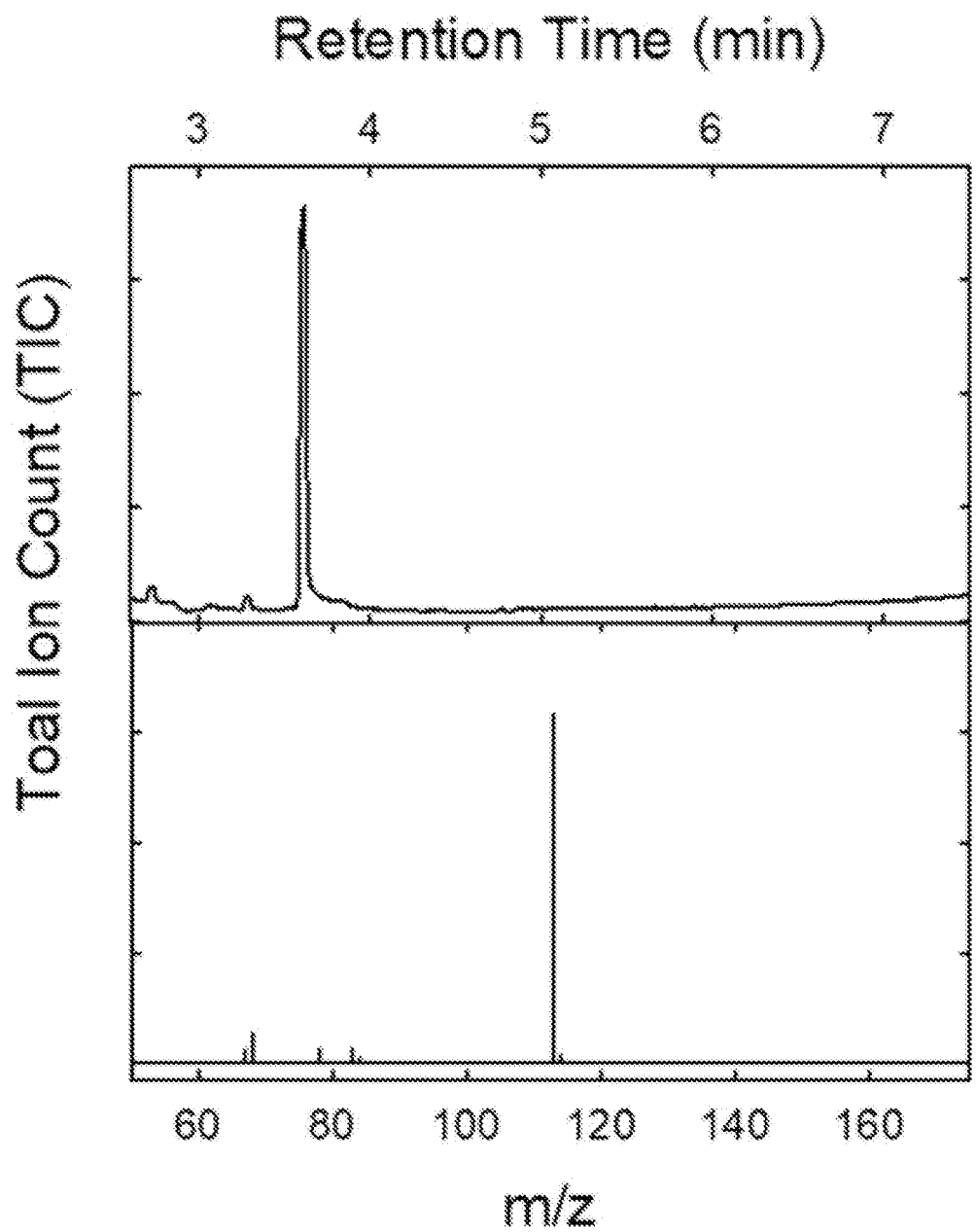
FIG. 5 presents a gas chromatogram (top) and mass spectrum (bottom) for the synthesis of 1-nitropyrazole produced from the continuous-flow reactor depicted by FIG. 4.

In a particular embodiment, 1-nitropyrazole (1-NP) may be isolated from the reaction mixture by precipitation of 1-nitropyrazole into crushed ice, followed by vacuum filtration and washing with cold deionized water. The overall reaction yield for a specific embodiment of this procedure was determined to be 97% from pyrazole. A gas chromatogram and mass spectrum for 1-nitropyrazole produced in a specific embodiment of this process design is shown in FIG. 5, where 1-nitropyrazole elutes at 3.6 minutes and the corresponding mass spectrum illustrates the compound eluting at the described retention time.

Figure 6:
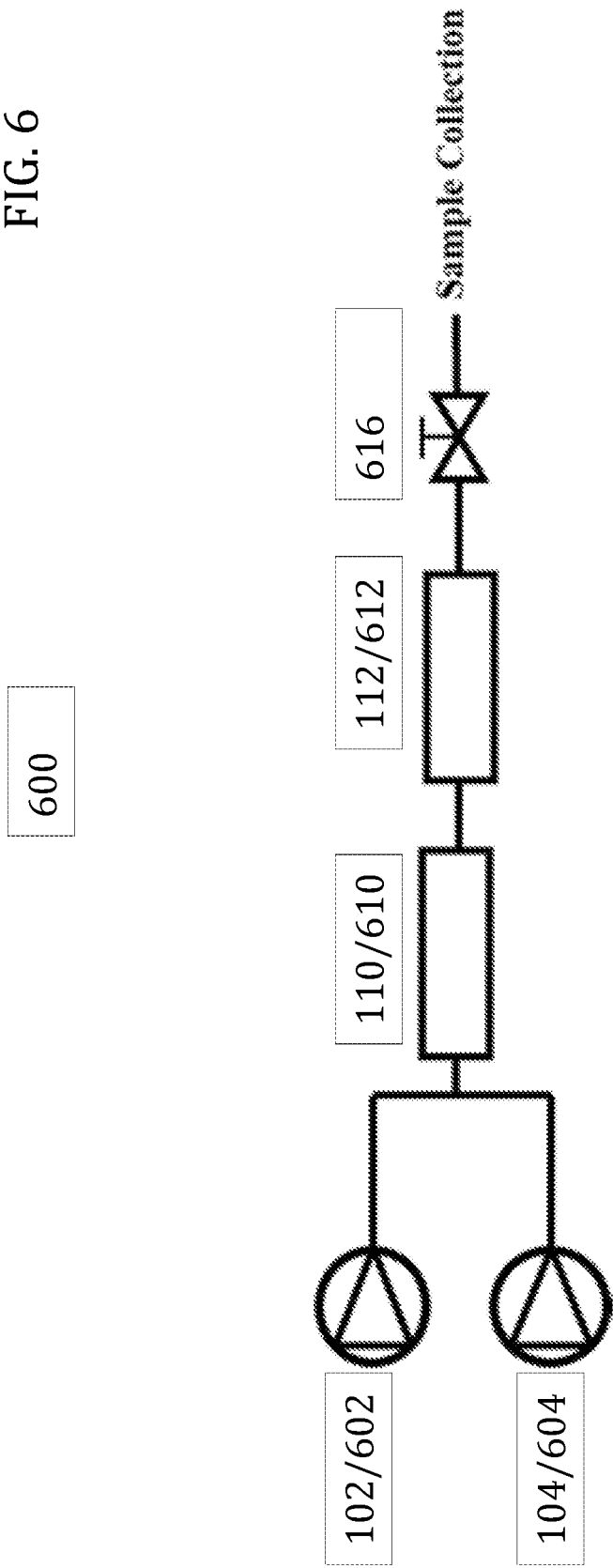
FIG. 6 presents a microfluidic reactor for the continuous flow synthesis of 3-nitropyrazole from pyrazole, according to an embodiment of the invention.
Figure 7:
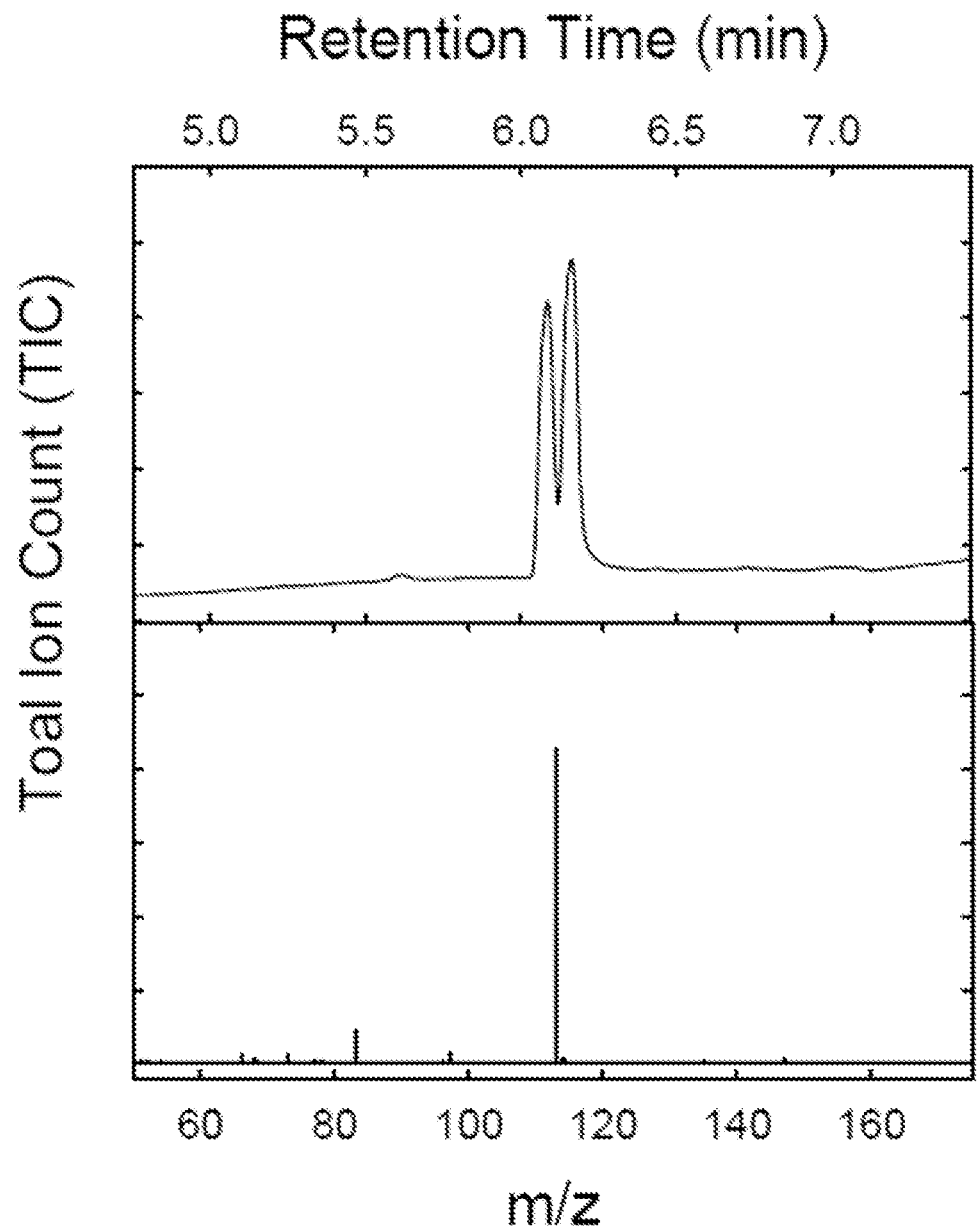
FIG. 7 presents a gas chromatogram (top) and mass spectrum (bottom) for the synthesis of 3-nitropyrazole produced from the continuous-flow reactor depicted by FIG. 6.

The 1-nitropyrazole produced in the method described in the previous paragraphs may also be used in the synthesis of 3-nitropyrazole in a continuous-flow design, as depicted in FIG. 6. In the case of the isolation of 3-nitropyrazole, the reactant mixture flowing from the microreactor 112/612 as depicted in FIG. 6 may be collected immediately following the rearrangement reaction. In a particular embodiment, the reaction conditions for the synthesis of 1-nitropyrazole in microreactor 110/610 are consistent with those described above with regard to FIG. 2. In a particular embodiment, the intermediate obtained from microreactor 110/610 is heated in microreactor 112/612 at temperatures of 110° C. to 180° C. and residence times within microreactor 110/610 greater than 15 minutes. The composition of microreactors 110/610 and 112/612 may be composed of materials able to withstand the highly acid and corrosive environments in addition to the thermal stress from heating the microreactors. In a particular embodiment, microreactors composed of glass or FEP tubing was sufficient for the selected temperature range. The microreactor 112/612 in FIG. 6 may have an internal diameter of 0.75 mm or larger. In a particular embodiment, microreactor 112/612 may have an internal diameter of 0.2-2.0 mm and is constructed from FEP tubing. An overall product yield for 3-nitropyrazole obtained in a specific embodiment was determined to be ~60%. The corresponding gas chromatogram for a particular embodiment is shown in FIG. 7 with 3-nitropyrazole eluting from the column at 6.1 minutes and 4-nitropyrazole eluting at 6.2 minutes. The mass spectrum for the 3-nitropyrazole compound eluting at 6.1 minutes is also shown in FIG. 7.

Alternatively, the 1-nitropyrazole synthesized in the microfluidic reactor described in the previous paragraphs may be used for a batch thermal rearrangement in a neat 1-nitropyrazole melt. In a particular embodiment, 1-nitropyrazole may be loaded into a batch reactor in the absence of any solvents and heated to temperatures ranging from 110-180° C., preferably between 150-170° C., or about 160° C. The reaction times required for the thermal rearrangement are between 15 min and 360 min. The batch reactor used for this rearrangement may be constructed from any material suitable to withstand the described temperatures, for example glass, stainless steel, Teflon, etc. After the described reaction time, the 3-nitropyrazole may be collected as a solid material and used for additional transformations.

Figure 8:
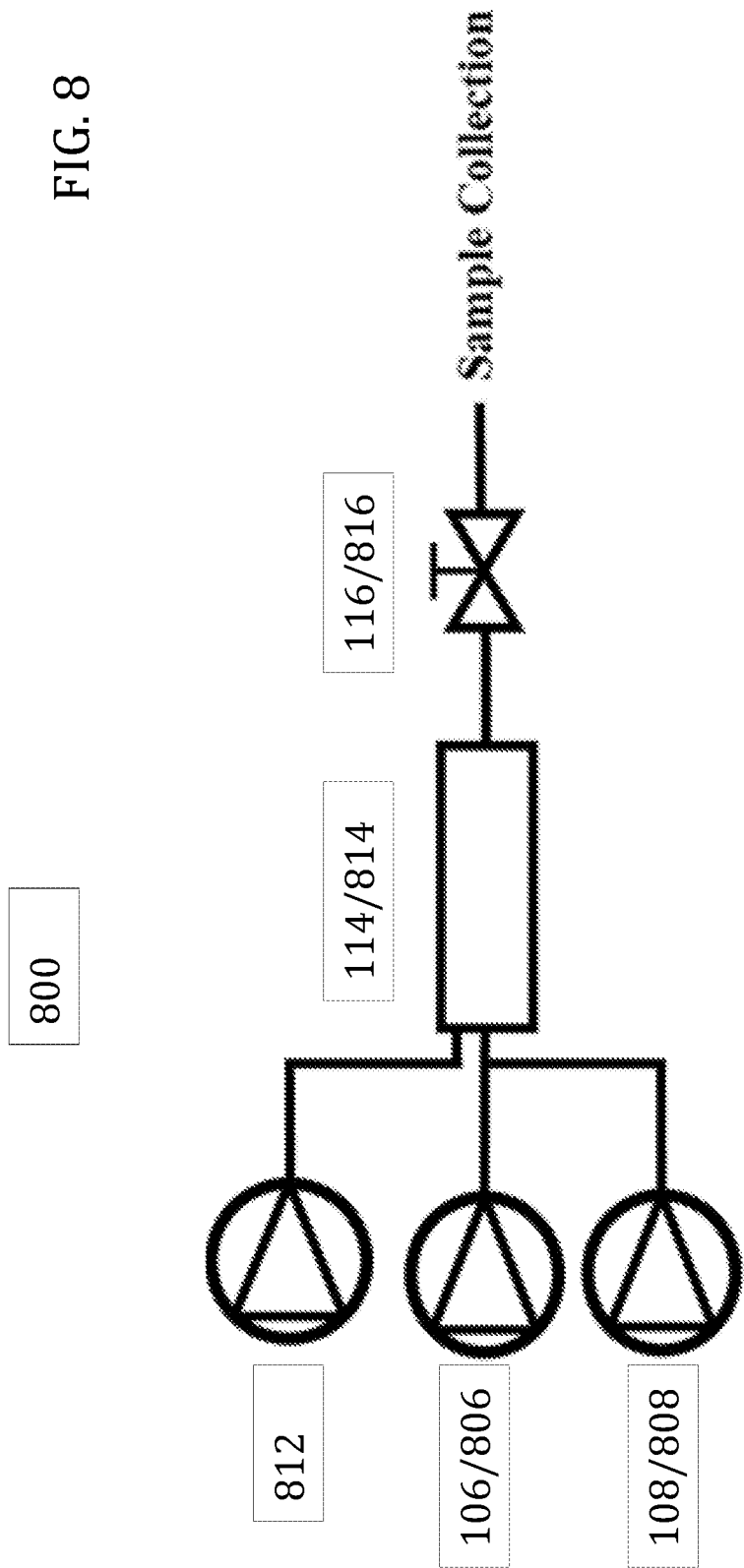
FIG. 8 presents a microfluidic reactor for the continuous flow synthesis of 3,4-nitropyrazole from 3-nitropyrazole, according to an embodiment of the invention.
Figure 9:
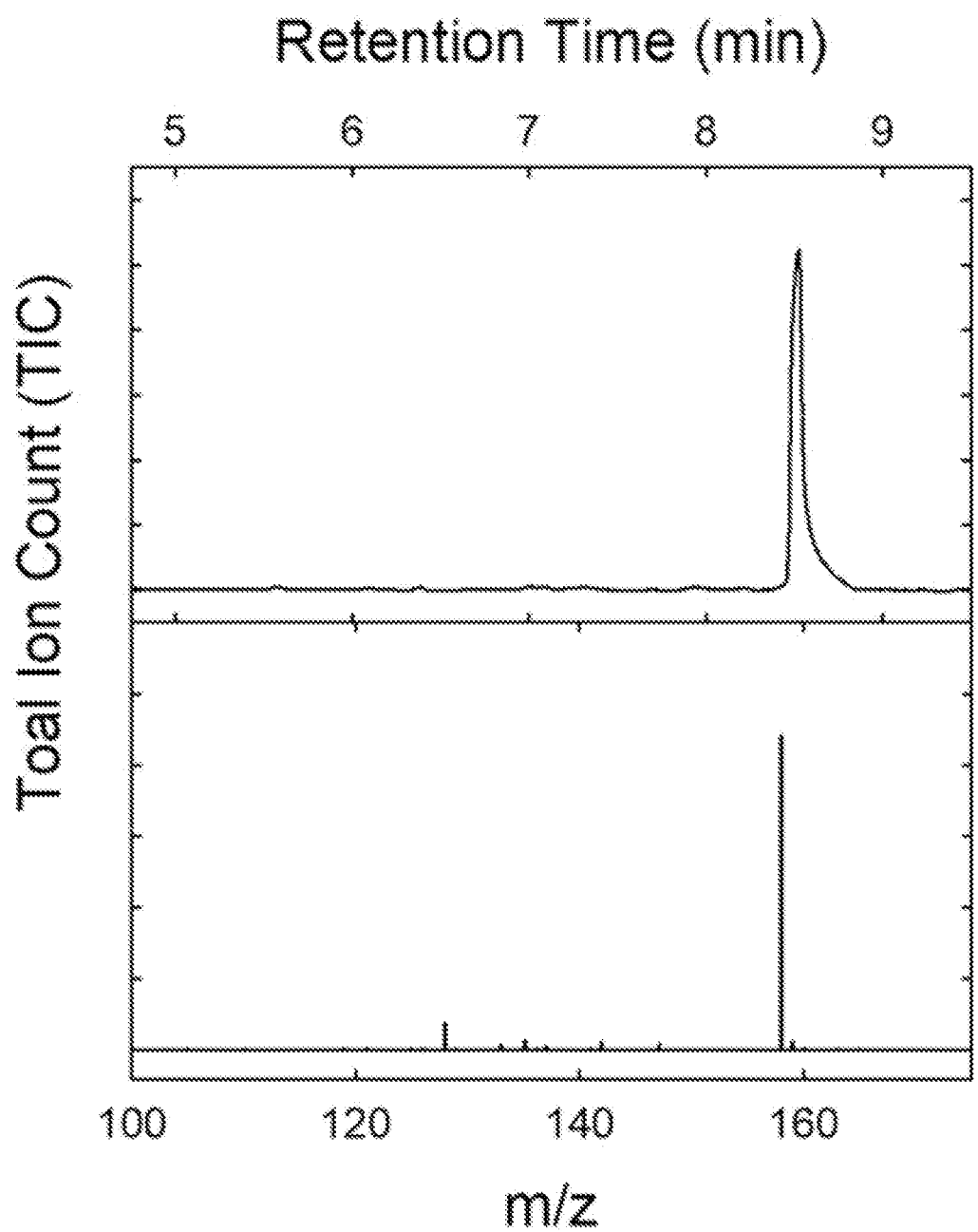
FIG. 9 presents a gas chromatogram (top) and mass spectrum (bottom) for the synthesis of 3,4-dinitropyrazole produced from the continuous-flow reactor depicted by FIG. 8.

The continuous-flow process for the 4-nitration of 3-nitropyrazole may be performed using the reaction mixture produced in the continuous-flow design disclosed herein or from commercially- or otherwise available 3-nitropyrazole. In a particular embodiment of this transformation, a reactor design 800 as illustrated in FIG. 8 is used, in which syringe/pump 812 is used for a 3-nitropyrazole solution in sulfuric acid or acetic acid:sulfuric acid mixtures. Furthermore, syringe/pumps 106/806 and 108/808 are designated for nitric acid and sulfuric acid respectively, which are premixed in-flow prior to reacting with 3-nitropyrazole with the microreactor 114/814. In a particular embodiment, the molar ratios of nitric acid:3-nitropyrazole are 1.0:1.0 to 5.0:1.0 and the molar ratios of sulfuric acid:nitric acid are 1.0:1.0 to 10.0:1.0, and the microreactor 114/814 is heated to between 25° C. to 80° C. In a particular embodiment, the microreactor design 800 is equipped with a BPR 116/816, as illustrated in FIG. 8, which is set to 1 to 5 bar, preferably 2 bar. The resulting reacting mixture eluting from the microreactor 800 as described may be isolated in-flow or manually by diluting with water and extracting with ethyl acetate. For the extraction, the solution may be diluted with water in-flow, extracted with an immiscible organic solvent, e.g. chloroform, ethyl acetate, hexanes, or diethyl ether, and separated by utilizing an in-flow separator to collect the organic phase. The resulting product was analyzed with gas chromatogram and mass spectrum, which can be seen in FIG. 9, in which 3,4-dinitropyrazole eluted at 8.5 minutes and which presents the corresponding mass spectrum for the compound eluting at this time.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A continuous flow microfluidic process comprising in a first microreactor, reacting a mixture of pyrazole:

and acetic anhydride with nitric acid to yield a first reaction solution comprising 1-nitropyrazole:

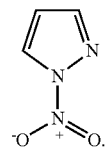

2. The continuous flow microfluidic process of claim 1, further comprising
in a second microreactor, thermally rearranging the 1-nitropyrazole to yield a second reaction solution comprising 3-nitropyrazole:

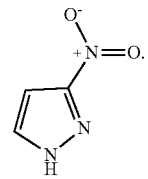

3. The continuous flow microfluidic process of claim 2, further comprising
in a third microreactor, reacting the 3-nitropyrazole with a mixture of nitric acid and sulfuric acid to yield a third reaction solution comprising 3,4-dinitropyrazole.

4. The continuous flow microfluidic process of claim 1, wherein the acetic anhydride solution further comprises acetic acid.

5. The continuous flow microfluidic process of claim 1, wherein the molar ratios of pyrazole:acetic anhydride are 1.0:1.0 to 2.0:1.0.

6. The continuous flow microfluidic process of claim 1, wherein the reaction is performed between 20-50° C.

7. The continuous flow microfluidic process of claim 1, further comprising collecting and isolating the 1-nitropyrazole.

8. The continuous flow microfluidic process of claim 1, wherein the molar ratio of nitric acid:pyrazole is 1.0:0.3 to 1.0:1.0.

9. The continuous flow microfluidic process of claim 2, wherein the thermal rearrangement is performed between 110-180° C.

10. The continuous flow microfluidic process of claim 2, further comprising collecting and isolating the 3-nitropyrazole.

11. The continuous flow microfluidic process of claim 3, further comprising collecting and isolating the 3,4-dinitropyrazole.

12. The continuous flow microfluidic process of claim 3, wherein the sulfuric acid is 98 wt % and the nitric acid is 100 wt %.

13. The continuous flow microfluidic process of claim 3, further comprising performing the reaction of the 3-nitropyrazole with the mixture of nitric acid and sulfuric acid to yield 3,4-dinitropyrazole at 25-80° C.

14. The continuous flow microfluidic process of claim 3, wherein the first, second, and third microreactors each have an inside diameter of between 0.2-1.0 mm.

15. The continuous flow microfluidic process of claim 3, wherein the first, second, and third microreactors are made from any of FEP (fluorinated ethylene propylene) tubing, FEP tubing with static helical mixers, and glass.

16. The continuous flow microfluidic process of claim 3, further comprising diluting the third reaction mixture containing 3,4-dinitropyrazole with deionized water and extracting the 3,4-dinitropyrazole with an immiscible organic solvent selected from the group consisting of chloroform, ethyl acetate, hexanes, and diethyl ether.

17. The continuous flow microfluidic process of claim 16, further comprising diluting and extracting the 3,4-dinitropyrazole in-flow.

18. The continuous flow microfluidic process of claim 6, wherein the reaction is performed between 20-30° C.

19. The continuous flow microfluidic process of claim 6, wherein the reaction is performed with a residence time of 0.17-10 minutes.

20. The continuous flow microfluidic process of claim 9, wherein the thermal rearrangement is performed between 110-180° C. for at least 15 minutes.

21. The continuous flow microfluidic process of claim 12, wherein the molar ratio of nitric acid:sulfuric acid is 1.0:1.0 to 1:10.

22. The continuous flow microfluidic process of claim 12, wherein the molar ratio of nitric acid:sulfuric acid is 1:5.

23. The continuous flow microfluidic process of claim 12, wherein the reaction of the 3-nitropyrazole with a mixture of nitric acid and sulfuric acid in the third microreactor includes a residence time of 1-10 minutes.

24. A continuous flow microfluidic process, comprising in a microreactor, thermally rearranging 1-nitropyrazole to yield a reaction solution comprising 3-nitropyrazole.

25. A continuous flow microfluidic process, comprising in a microreactor, reacting 3-nitropyrazole with a mixture of nitric acid and sulfuric acid to yield a reaction solution comprising 3,4-dinitropyrazole.

* * * * *